United States Patent
Leung et al.

(10) Patent No.: US 9,439,898 B2
(45) Date of Patent: Sep. 13, 2016

(54) METHODS FOR NOVEL DRUG DISCOVERY, TREATMENT AND SELECTIVE TARGETING FOR GEFITINIB-RESISTANT NON-SMALL-CELL LUNG CANCER HARBORING T790M MUTATION

(71) Applicant: Macau University of Science and Technology, Macau (MO)

(72) Inventors: Elaine Lai-Han Leung, Mo (MO); Liang Liu, Mo (MO); Xing-Xing Fan, Mo (MO)

(73) Assignee: Macau University of Science and Technology, Macau (MO)

( * ) Notice: Subject to any disclaimer, the term of this patent is extended or adjusted under 35 U.S.C. 154(b) by 0 days.

(21) Appl. No.: 14/296,477

(22) Filed: Jun. 5, 2014

(65) Prior Publication Data
US 2015/0297582 A1 Oct. 22, 2015

Related U.S. Application Data

(60) Provisional application No. 61/982,355, filed on Apr. 22, 2014.

(51) Int. Cl.
*C12Q 1/68* (2006.01)
*A61K 31/4741* (2006.01)
*A61K 33/40* (2006.01)
*G01N 33/50* (2006.01)

(52) U.S. Cl.
CPC ............ *A61K 31/4741* (2013.01); *A61K 33/40* (2013.01); *C12Q 1/6886* (2013.01); *G01N 33/5011* (2013.01); *C12Q 2600/136* (2013.01); *C12Q 2600/156* (2013.01); *G01N 2333/90209* (2013.01); *G01N 2333/91205* (2013.01)

(58) Field of Classification Search
CPC ............ A61K 31/4741; A61K 33/40; G01N 33/5011; G01N 2333/91205; C12Q 1/6886; C12Q 2600/136; C12Q 2600/156
See application file for complete search history.

(56) References Cited

PUBLICATIONS

Rungtabnapa et al., Hydrogen peroxide inhibits nonsmall cell lung cancer cell anoikis through the inhibition of caveolin-1 degradation, Am J Physiol Cell Physiol. Feb. 2011; 300(2): C235-C245.*
Gatti et al., Improved Apoptotic Cell Death in Drug-Resistant Non-Small-Cell Lung Cancer Cells by Tumor Necrosis Factor-Related Apoptosis-Inducing Ligand-Based Treatments, J Pharmacol Exp Ther 348:360-371, Mar. 2014.*
Lin et al. ("Lin"), "A High-throughput Cell-based Screening for L858R/T790M Mutant Epidermal Growth Factor Receptor Inhibitors," Anticancer Research 32: 147-152 (2012).*
A. Jemal et al. Cancer statistics 2010, CA: A Cancer Journal for Clinicians 2010, 60: 277-300.
A. Chang. Chemotherapy, chemoresistance and the changing treatment landscape for NSCLC, Lung Cancer 71 (2011) 3-10.

(Continued)

*Primary Examiner* — Reza Ghafoorian
(74) *Attorney, Agent, or Firm* — Ella Cheong Hong Kong; Sam T. Yip

(57) ABSTRACT

The present invention relates to methods for novel drug discovery, treatment and selective targeting for Gefitinib-resistant non-small-cell lung cancer (NSCLC) harboring an additional mutation, in particular, to the discovery of a drug candidate or agent identified by the presently claimed method for use in treating and selective targeting Gefitinib-resistant NSCLC harboring T790M mutation.

9 Claims, 12 Drawing Sheets

(56) References Cited

PUBLICATIONS

I. Y. Tam et al. Double EGFR mutants containing rare EGFR mutant types show reduced in vitro response to gefitinib compared with common activating missense mutations, Molecular Cancer Therapeutics 2009, 8: 2142-2151.

E. L. Leung et al. Src Promotes Survival and Invasion of Lung Cancers with Epidermal Growth Factor Receptor Abnormalities and is a Potential Candidate for Molecular-Targeted Therapy, Molecular Cancer Therapeutics 2009, 7: 923-932.

D. W. Wong et al. The EML4-ALK Fusion Gene is Involved in Various Histologic Types of Lung Cancers From Nonsmokers With Wild-type EGFR and KRAS, Cancer 2009, 115: 1723-33.

H. J. Jun et al. The Oncogenic Lung Cancer Fusion Kinase CD74-ROS Activates a Novel Invasiveness Pathway through E-Syt1 Phosphorylation, Cancer Research 2012, 72: 3764-3774.

O. Mayumi et al. Molecular Mechanisms of Epidermal Growth Factor Receptor (EGFR) Activation and Response to Gefitinib and Other EGFR-Targeting Drugs, Clinical Cancer Research 2006, 12: 7242-7251.

L. V. Sequist et al. Genotypic and Histological Evolution of Lung Cancers Acquiring Resistance to EGFR Inhibitors, Science translational medicine Mar. 23, 2011, 3(75): 75ra26.

T. K. Beuria et al. Sanguinarine Blocks Cytokinesis in Bacteria by Inhibiting FtsZ Assembly and Bundling, Biochemistry 2005, 44, 16584-16593.

B. W. Obiang-Obounou et al. The mechanism of action of sanguinarine against methicillin-resistant *Staphylococcus aureus*, The Journal of Toxicological Sciences, vol. 36, No. 3, 277-283, 2011.

K. Pencikova et al. Investigation of sanguinarine and chelerythrine effects on LPS-induced inflammatory gene expression in THP-1 cell line, Phytomedicine 19 (2012) 890-895.

X. Niu et al. The anti-inflammatory effects of sanguinarine and its modulation of inflammatory mediators from peritoneal macrophages, European Journal of Pharmacology 689 (2012) 262-269.

J. Vrba et al. Induction of heme oxygenase-1 by Macleaya cordata extract and its constituent sanguinarine in RAW264.7 cells, Fitoterapia 83 (2012) 329-335.

J. Vrba et al. Sanguinarine is a potent inhibitor of oxidative burst in DMSO-differentiated HL-60 cells by a non-redox mechanism, Chemico-Biological Interactions 147 (2004) 35-47.

L. Bai et al. Site-specific binding of chelerythrine and sanguinarine to single pyrimidine bulges in hairpin DNA Analytical and bioanalytical chemistry (2008) 392:709-716.

\* cited by examiner

Only transfectant with T790M-containing constructs showed EGFR degradation after both sanguinarine and $H_2O_2$ treatment.

D.

SEQUENCE LISTING

```
<160> NUMBER OF SEQ ID NOS: 2

<210> SEQ ID NO 1
<211> LENGTH: 3633
<212> TYPE: DNA
<213> ORGANISM: Human

<400> SEQUENCE: 1
atgcgaccct ccgggacggc cggggcagcg ctcctggcgc tgctggctgc gctctgcccg    60
```

```
gcgagtcggg ctctggagga aaagaaagtt tgccaaggca cgagtaacaa gctcacgcag    120
ttgggcactt ttgaagatca ttttctcagc ctccagagga tgttcaataa ctgtgaggtg    180
gtccttggga atttggaaat tacctatgtg cagaggaatt atgatctttc cttcttaaag    240
accatccagg aggtggctgg ttatgtcctc attgccctca acacagtgga gcgaattcct    300
ttggaaaacc tgcagatcat cagaggaaat atgtactacg aaaattccta tgccttagca    360
gtcttatcta actatgatgc aaataaaacc ggactgaagg agctgcccat gagaaattta    420
caggaaatcc tgcatggcgc cgtgcggttc agcaacaacc ctgccctgtg caacgtggag    480
agcatccagt ggcgggacat agtcagcagt gactttctca gcaacatgtc gatggacttc    540
cagaaccacc tgggcagctg ccaaaagtgt gatccaagct gtcccaatgg agctgctgg     600 ggtgcaggag aggagaactg ccagaaactg accaaaatca tctgtgccca gcagtgctcc    660
gggcgctgcc gtggcaagtc ccccagtgac tgctgccaca accagtgtgc tgcaggctgc    720
acaggccccc gggagagcga ctgcctggtc tgccgcaaat ccgagacga  agccacgtgc    780 aaggacacct gcccccact  catgctctac aaccccacca cgtaccagat ggatgtgaac    840
cccgagggca atacagcttt tggtgccacc tgcgtgaaga agtgtcccg  taattatgtg    900 gtgacagatc acggctcgtg cgtccgagcc tgtggggccg acagctatga gatggaggaa    960
gacggcgtcc gcaagtgtaa gaagtgcgaa gggccttgcc gcaaagtgtg taacggaata   1020
ggtattggtg aatttaaaga ctcactctcc ataaatgcta cgaatattaa acacttcaaa   1080
aactgcacct ccatcagtgg cgatctccac atcctgccgg tggcatttag gggtgactcc   1140
ttcacacata ctcctcctct ggatccacag gaactggata ttctgaaaac cgtaaaggaa   1200
atcacagggt ttttgctgat tcaggcttgg cctgaaaaca ggacggacct ccatgccttt   1260
gagaacctag aaatcatacg cggcaggacc aagcaacatg gtcagttttc tcttgcagtc   1320
gtcagcctga acataacatc cttgggatta cgctccctca aggagataag tgatggagat   1380
gtgataattt caggaaacaa aaatttgtgc tatgcaaata caataaactg gaaaaaactg   1440
tttgggacct ccggtcagaa aaccaaaatt ataagcaaca gaggtgaaaa cagctgcaag   1500
gccacaggcc aggtctgcca tgccttgtgc tcccccgagg gctgctgggg cccggagccc   1560
agggactgcg tctcttgccg gaatgtcagc cgaggcaggg aatgcgtgga caagtgcaac   1620
cttctggagg gtgagccaag ggagtttgtg gagaactctg agtgcataca gtgccaccca   1680
gagtgcctgc ctcaggccat gaacatcacc tgcacaggac ggggaccaga caactgtatc   1740
cagtgtgccc actacattga cggccccac  tgcgtcaaga cctgcccggc aggagtcatg   1800
ggagaaaaca caccctggt  ctggaagtac gcagacgccg gccatgtgtg ccacctgtgc   1860
catccaaact gcacctacgg atgcactggg ccaggtcttg aaggctgtcc aacgaatggg   1920
cctaagatcc cgtccatcgc cactgggatg gtgggggccc tcctcttgct gctggtggtg   1980
gccctgggga tcggcctctt catgcgaagg cgccacatcg ttcggaagcg cacgctgcgg   2040
aggctgctgc aggagaggga gcttgtggag cctcttacac ccagtggaga agctcccaac   2100
caagctctct tgaggatctt gaaggaaact gaattcaaaa agatcaaagt gctgggctcc   2160
ggtgcgttcg gcacggtgta aagggactc  tggatcccag aaggtgagaa agttaaaatt   2220
cccgtcgcta tcaaggaatt aagagaagca acatctccga aagccaacaa ggaaatcctc   2280
gatgaagcct acgtgatggc cagcgtggac aaccccacg  tgtgccgcct gctgggcatc   2340
tgcctcacct ccaccgtgca gctcatcacg cagctcatgc ccttcggctg cctcctggac   2400
```

```
tatgtccggg aacacaaaga caatattggc tcccagtacc tgctcaactg gtgtgtgcag    2460
atcgcaaagg gcatgaacta cttggaggac cgtcgcttgg tgcaccgcga cctggcagcc    2520
aggaacgtac tggtgaaaac accgcagcat gtcaagatca cagattttgg gctggccaaa    2580
ctgctgggtg cggaagagaa agaataccat gcagaaggag gcaaagtgcc tatcaagtgg    2640
atggcattgg aatcaatttt acacagaatc tatacccacc agagtgatgt ctggagctac    2700
ggggtgaccg tttgggagtt gatgaccttt ggatccaagc catatgacgg aatccctgcc    2760
agcgagatct cctccatcct ggagaaagga gaacgcctcc ctcagccacc catatgtacc    2820
atcgatgtct acatgatcat ggtcaagtgc tggatgatag acgcagatag tcgcccaaag    2880
ttccgtgagt tgatcatcga attctccaaa atggcccgag accccagcg ctaccttgtc    2940 attcaggggg atgaaagaat gcatttgcca agtcctacag actccaactt ctaccgtgcc    3000
ctgatggatg aagaagacat ggacgacgtg gtggatgccg acgagtacct catcccacag    3060
cagggcttct tcagcagccc ctccacgtca cggactcccc tcctgagctc tctgagtgca    3120
accagcaaca attccaccgt ggcttgcatt gatagaaatg ggctgcaaag ctgtccatc    3180 aaggaagaca gcttcttgca gcgatacagc tcagacccca caggcgcctt gactgaggac    3240
agcatagacg acaccttcct cccagtgcct gaatacataa accagtccgt tcccaaaagg    3300
cccgctggct ctgtgcagaa tcctgtctat cacaatcagc ctctgaaccc cgcgcccagc    3360
agagacccac actaccagga cccccacagc actgcagtgg caaccccga gtatctcaac    3420 actgtccagc ccacctgtgt caacagcaca ttcgacagcc ctgcccactg ggcccagaaa    3480
ggcagccacc aaattagcct ggacaaccct gactaccagc aggacttctt tcccaaggaa    3540
gccaagccaa atggcatctt taagggctcc acagctgaaa atgcagaata cctaagggtc    3600
gcgccacaaa gcagtgaatt tattggagca tga                                 3633
```

<210> SEQ ID NO 2
<211> LENGTH: 1210
<212> TYPE: PRT
<213> ORGANISM: Human

<400> SEQUENCE: 2

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
        50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

-continued

```
Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575
```

-continued

```
Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
            645                 650                 655

Leu Leu Val Val Ala Leu Gly Ile Gly Leu Phe Met Arg Arg Arg His
        660                 665                 670

Ile Val Arg Lys Arg Thr Leu Arg Arg Leu Leu Gln Glu Arg Glu Leu
    675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
            725                 730                 735

Lys Val Lys Ile Pro Val Ala Ile Lys Glu Leu Arg Glu Ala Thr Ser
        740                 745                 750

Pro Lys Ala Asn Lys Glu Ile Leu Asp Glu Ala Tyr Val Met Ala Ser
    755                 760                 765

Val Asp Asn Pro His Val Cys Arg Leu Leu Gly Ile Cys Leu Thr Ser
770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
            805                 810                 815

Trp Cys Val Gln Ile Ala Lys Gly Met Asn Tyr Leu Glu Asp Arg Arg
        820                 825                 830

Leu Val His Arg Asp Leu Ala Ala Arg Asn Val Leu Val Lys Thr Pro
    835                 840                 845

Gln His Val Lys Ile Thr Asp Phe Gly Leu Ala Lys Leu Leu Gly Ala
    850                 855                 860

Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
            885                 890                 895

Val Trp Ser Tyr Gly Val Thr Val Trp Glu Leu Met Thr Phe Gly Ser
        900                 905                 910

Lys Pro Tyr Asp Gly Ile Pro Ala Ser Glu Ile Ser Ser Ile Leu Glu
    915                 920                 925

Lys Gly Glu Arg Leu Pro Gln Pro Pro Ile Cys Thr Ile Asp Val Tyr
930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
            965                 970                 975

Arg Tyr Leu Val Ile Gln Gly Asp Glu Arg Met His Leu Pro Ser Pro
        980                 985                 990

Thr Asp Ser Asn Phe Tyr Arg Ala  Leu Met Asp Glu Glu  Asp Met Asp
```

```
                  995                  1000                 1005
Asp Val Val Asp Ala Asp Glu Tyr Leu Ile Pro Gln Gln Gly Phe
    1010                1015                1020

Phe Ser Ser Pro Ser Thr Ser Arg Thr Pro Leu Leu Ser Ser Leu
    1025                1030                1035

Ser Ala Thr Ser Asn Asn Ser Thr Val Ala Cys Ile Asp Arg Asn
    1040                1045                1050

Gly Leu Gln Ser Cys Pro Ile Lys Glu Asp Ser Phe Leu Gln Arg
    1055                1060                1065

Tyr Ser Ser Asp Pro Thr Gly Ala Leu Thr Glu Asp Ser Ile Asp
    1070                1075                1080

Asp Thr Phe Leu Pro Val Pro Glu Tyr Ile Asn Gln Ser Val Pro
    1085                1090                1095

Lys Arg Pro Ala Gly Ser Val Gln Asn Pro Val Tyr His Asn Gln
    1100                1105                1110

Pro Leu Asn Pro Ala Pro Ser Arg Asp Pro His Tyr Gln Asp Pro
    1115                1120                1125

His Ser Thr Ala Val Gly Asn Pro Glu Tyr Leu Asn Thr Val Gln
    1130                1135                1140

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
    1190                1195                1200

Ser Ser Glu Phe Ile Gly Ala
    1205                1210
```

METHODS FOR NOVEL DRUG DISCOVERY, TREATMENT AND SELECTIVE TARGETING FOR GEFITINIB-RESISTANT NON-SMALL-CELL LUNG CANCER HARBORING T790M MUTATION

CROSS REFERENCE TO RELATED APPLICATION

Pursuant to 35 U.S.C. §119(e), this is a non-provisional patent application which claims benefit from U.S. provisional patent application Ser. No. 61/982,355 filed Apr. 22, 2014, and the disclosure of which is incorporated herein by reference in its entirety.

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

The present invention relates to methods for novel drug discovery, treatment and selective targeting for Gefitinib-resistant non-small-cell lung cancer (NSCLC) harboring an additional mutation, in particular, to the discovery of a drug candidate or agent identified by the presently claimed method for use in treating and selective targeting Gefitinib-resistant NSCLC harboring T790M mutation.

BACKGROUND OF THE INVENTION

Lung cancer is the leading cause of cancer deaths globally [1]. Non-small-cell lung cancer (NSCLC) accounts for over 80% of all the histological classified lung cancer cases, and patients are often diagnosed at the advanced stages of the disease, therefore the prognosis of lung cancer remains poor [2]. With the advanced development of DNA sequencing technology, the therapeutic strategy of NSCLC has been modified towards to personalized therapy. Some specific driver genetic mutations have been identified in NSCLC, such as EGFR [3, 4], EML4-ALK fusion gene [5] and ROS fusion gene [6], which directs the development of molecular-targeted drug discovery to target theses mutations. Among those mutations, EGFR mutation is the most frequently observed gene mutation in Eastern Oriental population, especially in subgroup of patients who are non-smoker, female, clinically diagnosed with Adenocarcinoma and early onset. The common activating mutation of EGFR is a substitution mutation of $EGFR^{L858R}$, which makes EGFR constitutively activated even without EGF stimulation, resulting in downstream activation of anti-apoptotic signaling. Gefitinib, which is a tyrosine kinase inhibitor (TKI), can specifically inhibit EGFR as well as its downstream survival signaling pathway [7]. However, despite the initial significant responses to Gefitinib treatment, like other chemotherapeutic agents, patients acquire resistance to Gefitinib ultimately, and the median time to disease progression is just about 12 months [8]. The most common reasons of Gefitinib resistance is the presence of additional EGFR mutation ($EGFR^{L858R+T790M}$), which accounts for over 49% of all the resistance cases. The additional T790M mutation will provide steric hindrance to TKI due to the bulkiness of Methionine (M), thus the overall pharmaceutical effect of Gefitinib is weakened. Therefore, it is an urgent need to identify EGFR crosstalk pathways and to discover more effective agents as new candidate drugs for Gefitinib-resistant NSCLC patients.

Sanguinarine, a benzophenanthridine alkaloid, can be isolated from Chinese medicinal herb *Macleaya cordata* or from North American herb *sanguinaria canadensis*. *Macleaya cordata* injection has been utilized as clinical application for treating inflammation. As a major constituent, the pharmacological effects of sanguinarine have been widely studied in many fields for a long time, for example, as anti-microbe [9, 10], anti-inflammation [11, 12] and anti-oxidation [13, 14], but not in the field of NSCLC, especially on Gefitinib-resistant NSCLC. It has acquired the FDA approval as an antibacterial or antiplaque agent in toothpastes in 2003 [15]. Using the drug discovery method as disclosed in the present invention demonstrates the cytotoxic potency of sanguinarine and other chemical agent in treating and selectively targeting Gefitinib-resistant NSCLC. In the present invention, methods for treating and selectively targeting a specific Gefitinib-resistant NSCLC which harbors an additional mutation by using sanguinarine and at least one chemical agent will also be disclosed.

SUMMARY OF THE INVENTION

Accordingly, an objective of the present invention is to provide a method for treating and selectively targeting NSCLC harboring T790M mutation on EGFR comprising using a compound and at least a chemical agent which can elevate high level of reaction oxygen species (ROS) to selectively induce cytotoxicity in gefitinib-resistant NSCLC having T790M additional mutation. According to an embodiment of the present invention, five NSCLC cell lines with different EGFR statuses and gefitinib sensitivity are used to examine the cytotoxic potency of sanguinarine and a chemical agent, e.g. $H_2O_2$. One of the five cell lines, H1975, which contains L858R and T790M double mutation on EGFR is a gefitinib-resistant NSCLC cell line. H1975 cells demonstrate the highest sensitivity to the treatment of sanguinarine among the five cell lines. The $IC_{50}$ value of H1975 for sanguinarine is much higher than that of another cell line, A549, which contains wild-type of EGFR. Moreover, the increase of ROS induced by sanguinarine through the up-regulation and activation of NOX3 specifically and significantly induces the degradation of EGFR in H1975 cells. Using $H_2O_2$ or any other agents that can elevate ROS also specifically induces EGFR degradation and apoptosis, indicating that $H_2O_2$ is a promising chemical agent for treating T790M containing gefitinib-resistant NSCLC. Another factor contributes to the sensitivity of H1975 upon sanguinarine treatment is methionine sulfoxide reductase. Compared with the normal lung epithelial cells, expression of the methionine sulfoxide reductase is at the lowest level in H1975 cells among the five cell lines. Therefore, the increase of ROS induced by sanguinarine is much easier to push H1975 onto the limit of oxidative stress and then induces apoptosis than that in other NSCLC cell lines. The screening method of the present invention can also be used to test other compound or agent in future for specifically treating gefitinib-resistant NSCLC having additional mutation such as T790M.

BRIEF DESCRIPTION OF THE DRAWINGS

Embodiments of the present invention are described in more detail hereinafter with reference to the drawings, in which.

DETAILED DESCRIPTION OF THE INVENTION

The following description and the corresponding embodiments of the present invention are set forth as preferred examples. It will be apparent to those skilled in the art that modifications, including additions and/or substitutions, may be made without departing from the scope and spirit of the invention. Specific details may be omitted so as not to obscure the invention; however, the disclosure is written to enable one skilled in the art to practice the teachings herein without undue experimentation.

EXAMPLES

Example 1

$IC_{50}$ Values of Sanguinarine Against Five NSCLC Cell Lines

Table 1 shows $I_{C50}$ values of sanguinarine against five NSCLC cell lines. Among the five cell lines, H1975 is the most sensitive cells to sanguinarine treatment, while A549 is the most resistant one. The $IC_{50}$ value of sanguinarine in H1975 is 3-fold, 8-fold, 5.1-fold and 5.4-fold lower than that of HCC827, A549, H1650 and H2228 respectively, suggesting that sanguinarine is especially more effective in NSCLC cells containing EGFR L858R+T790M double mutation.

TABLE 1

$IC_{50}$ values of sanguinarine against five NSCLC cell lines.

| Cell lines | $IC_{50}$ value (µM) | | Gefitinib resistance |
|---|---|---|---|
| | Treatment (24 hrs) | Treatment (48 hrs) | |
| H1975(EGFR$^{L858R+T790M}$) | 0.68 ± 0.24 | 0.58 ± 0.14 | resistance |
| HCC827(EGFR$^{L858R}$) | 1.90 ± 0.248 | 1.055 ± 0.27 | sensitive |
| H1650 (EGFR$^{Exon19\ deletion}$) | 3.47 ± 1.31 | 2.64 ± 1.31 | resistance |
| H2228 (EML4-ALK) | 3.73 ± 1.23 | 3.08 ± 1.56 | resistance |
| A549 (EGFR$^{wild-type}$) | 5.71 ± 1.73 | 3.83 ± 1.11 | resistance |

Example 2

Reactive Oxygen Species (ROS) Generation Induced by Sanguinarine in H1975 Cells

Figure 1:
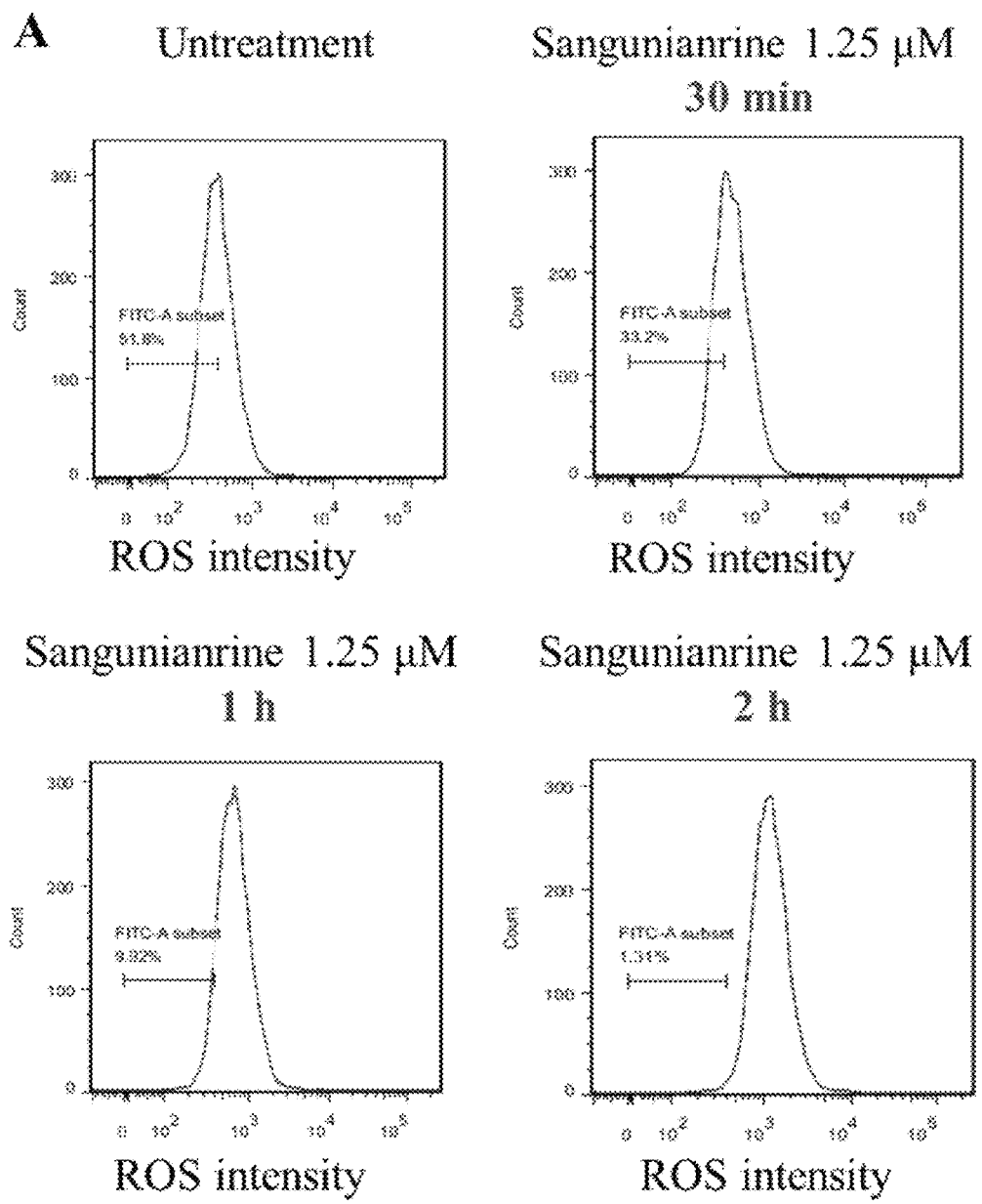
FIG. 1 is flow cytometry plots depicting ROS content induced by different concentration of sanguinarine in H1975 cells.
Figure 1:
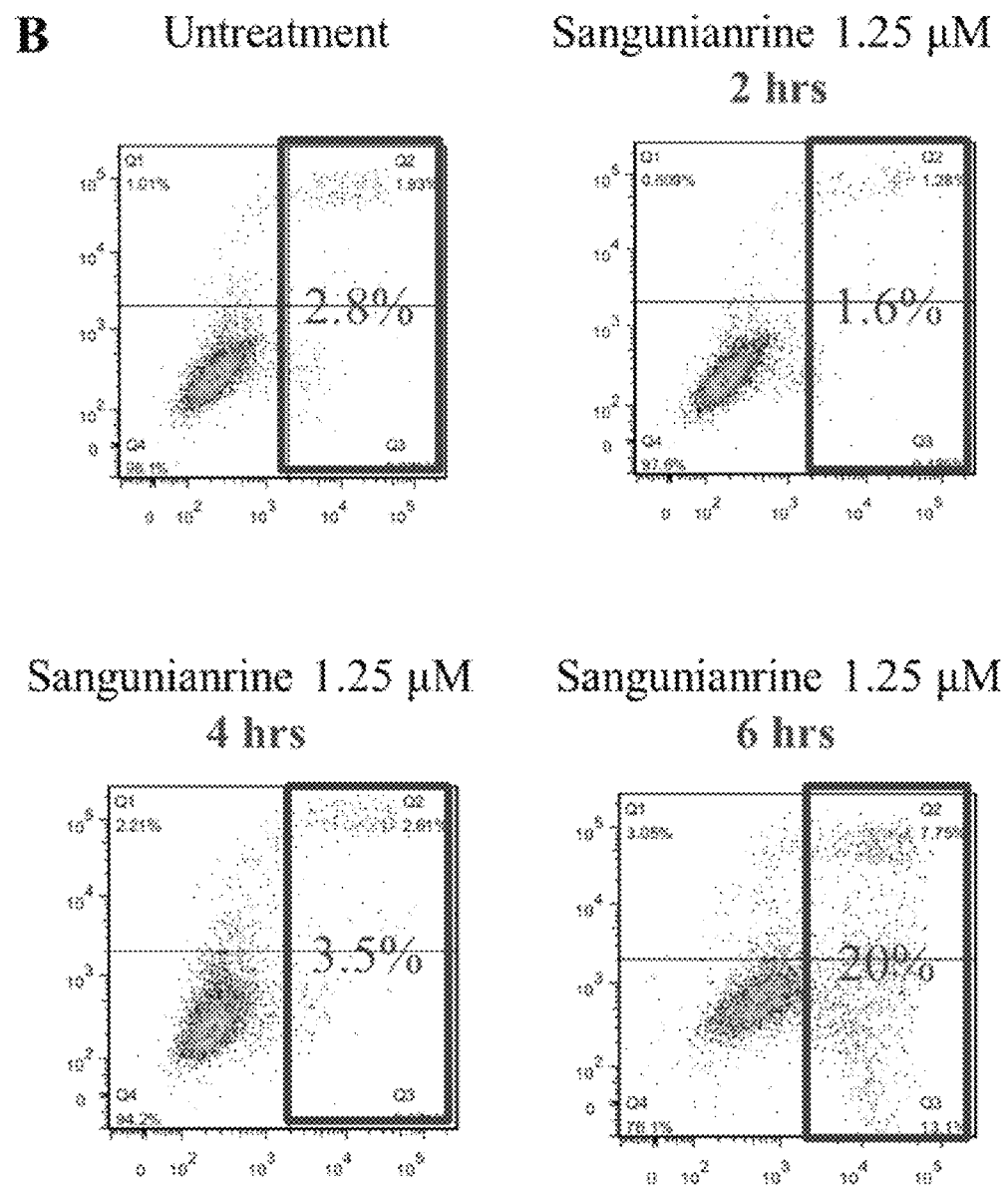

ROS generation is an early and essential response to apoptosis induced by sanguinarine. Therefore, according to example 1, H1975 cells are selected as the cell model of NSCLC cells containing EGFR L858R+T790M double mutation to evaluate the efficacy of sanguinarine in induction of ROS generation. Flow cytometry is used to study ROS intensity in H1975 cells treated with 1.25 µM sanguinarine over a time course. In FIG. 1A, ROS generation is induced by sanguinarine starting at 30 minutes of incubation, and gradually increased over the time course. FIG. 1B shows that from 4 hours to 6 hours of sanguinarine treatment, the ROS generation is increased more significantly.

Example 3

Figure 2:
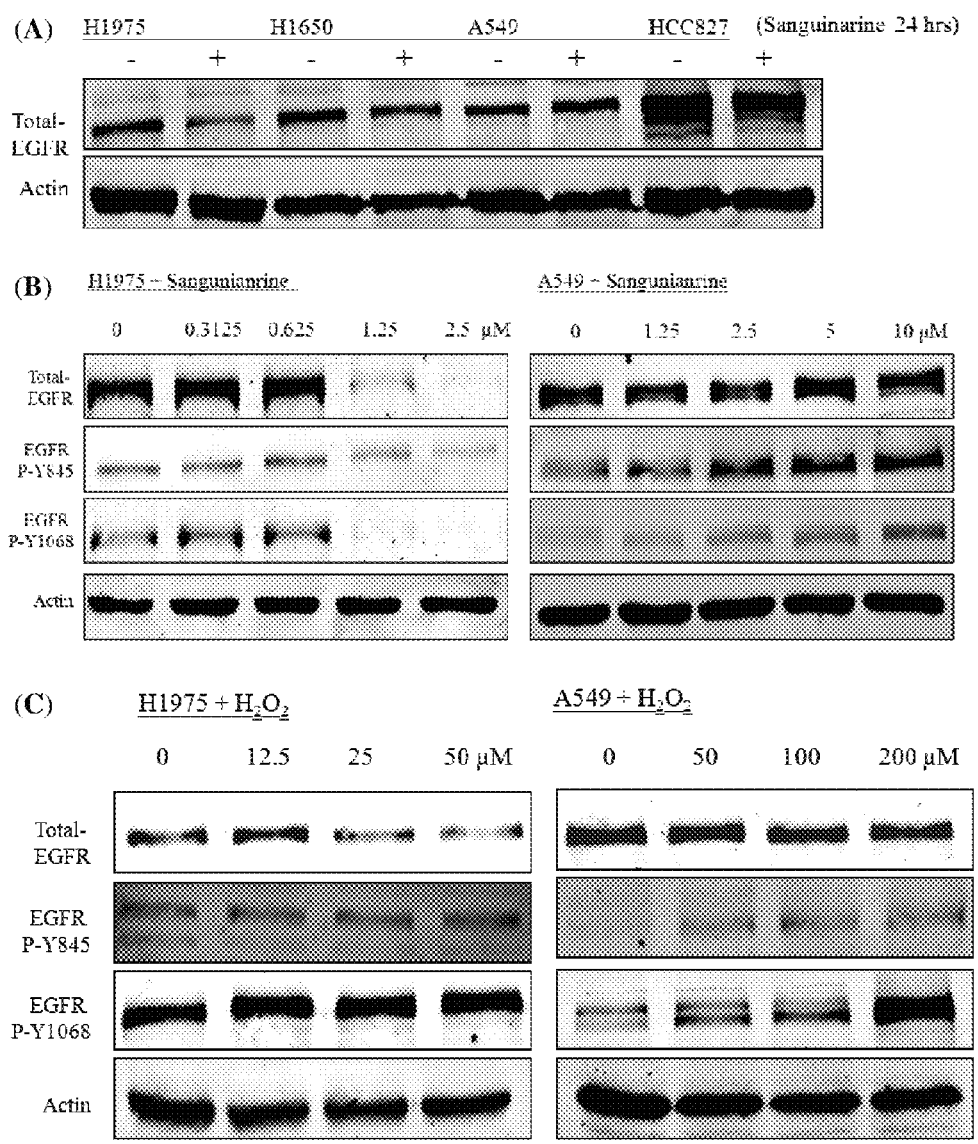
FIG. 2 is western blots of different EGFR markers in different cell lines treated with sanguinarine (A), H1975 and A549 cells treated with different concentrations of sanguinarine (B), and H1975 and A549 cells treated with different concentrations of $H_2O_2$.

Effect of Elevation of ROS Induced by Sanguinarine or $H_2O_2$ on EGFR Degradation in NSCLC Cells with T790M Mutation In FIG. 2, expression level of total EGFR, EGFR (pY845) and EGFR (pY1068) in different NSCLC cell lines (H1975, H1650, A594, and HCC827) treated with different concentrations of sanguinarine (FIG. 2B) and $H_2O_2$ (FIG. 2C) is demonstrated. FIG. 2A is a control. Among the four cell lines, only H1975 cells have additional T790M mutation on EGFR. At 1.25 µM sanguinarine, expression level of total EGFR, pY845 EGFR and pY1068 EGFR is all reduced in H1975 cells; whereas no significant reduction in expression level of all markers by sanguinarine is observed in A594 cells. Compared with sanguinarine, effect of $H_2O_2$ on suppression of these markers in H1975 cells is relatively less significant. However, at 25 µM $H_2O_2$, expression level of total EGFR and pY845 EGFR appears to be slightly reduced in H1975 cells; whereas no significant change in the level of all markers in A594 cells by $H_2O_2$ is observed. This example reveals that both sanguinarine and $H_2O_2$ can degrade EGFR but their cytotoxic potency are different. Sanguinarine is more potent than $H_2O_2$ in terms of the EGFR degradation in NSCLC cells having T790M mutation and the concentration used. The EGFR degradation is also specific in NSCLC cells having T790M mutation by using sanguinarine or $H_2O_2$.

Example 4

Effect of Sanguinarine or H₂O₂ on EGFR T790M Transfected Cells

Figure 3:
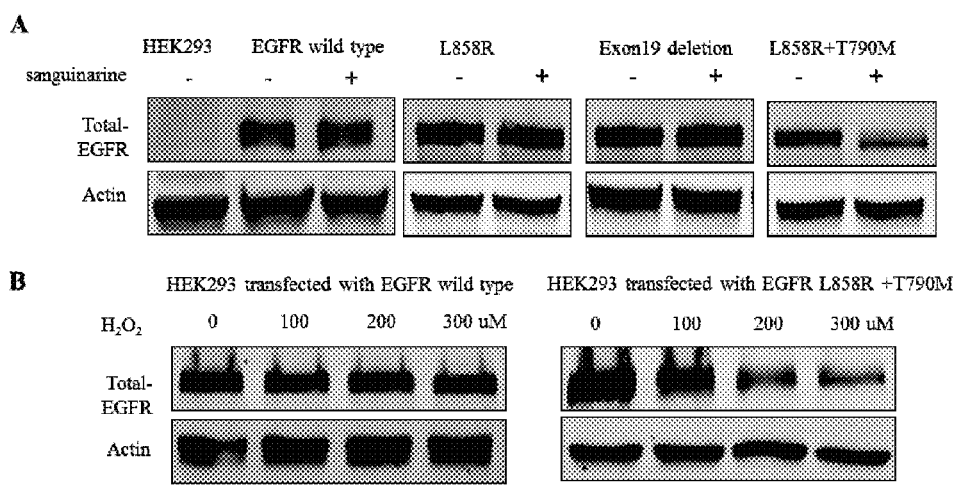
FIG. 3 is western blots of different EGFR markers in HEK293 cells transfected with different constructs and treated with sanguinarine (A) and $H_2O_2$ (B); (A) from left to right: HEK293 cells, HEK293 cells with wild type EGFR, HEK293 cells with L858R mutation on EGFR, HEK293 cells with exon 19 deletion on EGFR, HEK293 cells with double mutation of L858R and T790M on EGFR; (B) left panel: HEK293 cells with wild type EGFR treated with 0, 100, 200 and 300 µM $H_2O_2$; right panel: HEK293 cells with double mutation of L858R and T790M on EGFR treated with 0, 100, 200 and 300 µM $H_2O_2$.

HEK293 cells are used in this example as cell model to be transfected with different constructs of EGFR (wild-type, L858R mutation, Exon 19 deletion, L858R+T790M double mutation). In FIG. 3A, 3 µM saguinarine is added into the HEK293 transfected with different EGFR constructs. Expression level of total EGFR in different samples of HEK293 cells is shown in western blot, where the HEK293 cells transfected with EGFR construct having double mutation (L858R and T790M) (SEQ. ID NO. 1/GenBank Accession number of DNA is NM_005228) shows significant reduction in total EGFR level, while the rest of the samples do not show any significant reduction in total EGFR level. FIG. 3B shows expression level of total EGFR in different HEK293 cell samples treated with different concentrations of $H_2O_2$. In HEK293 cells transfected with construct of EGFR having double mutation, sample treated with 200 µM $H_2O_2$ shows significant reduction in total EGFR level; sample treated with 300 µM $H_2O_2$ even shows a more significant reduction in total EGFR level. This example reveals that both Sanguinarine and ROS elevating agents such as $H_2O_2$ can specifically induce EGFR degradation not only in cell line but also in EGFR T790M transfectant, indicating that the ROS-induced EGFR degradation effect is a new mechanism related to the unique character of T790M mutation on EGFR rather than individual cell line character.

Example 5

Figure 4:
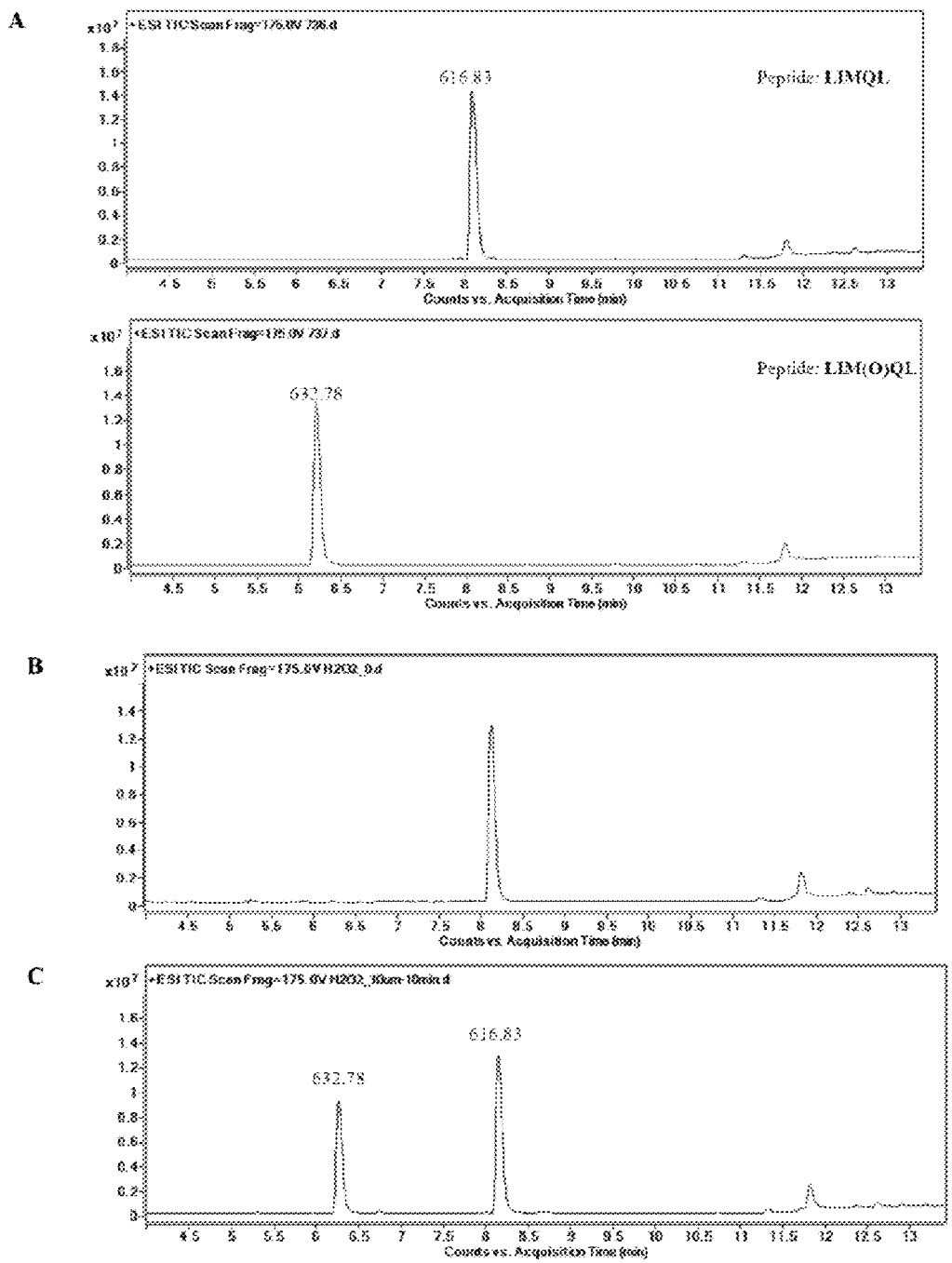
FIG. 4 is ESI-MS result of short peptide and oxidized methionine in the peptide treated with different concentrations of $H_2O_2$: (A) peptide of LIMQL and its oxidized form, LIM(O)QL; (B) is $H_2O_2$ untreated sample; (C) is sample treated with 10 µM $H_2O_2$ for 10 min; (D) is sample treated with 20 µM $H_2O_2$ for 10 min; (E) is sample treated with 40 µM $H_2O_2$ for 10 min; (F) is sample treated with 80 µM $H_2O_2$ for 10 min; (G) is sample treated with 100 µM $H_2O_2$ for 10 min; One of representative data was shown (n=3)
Figure 4:
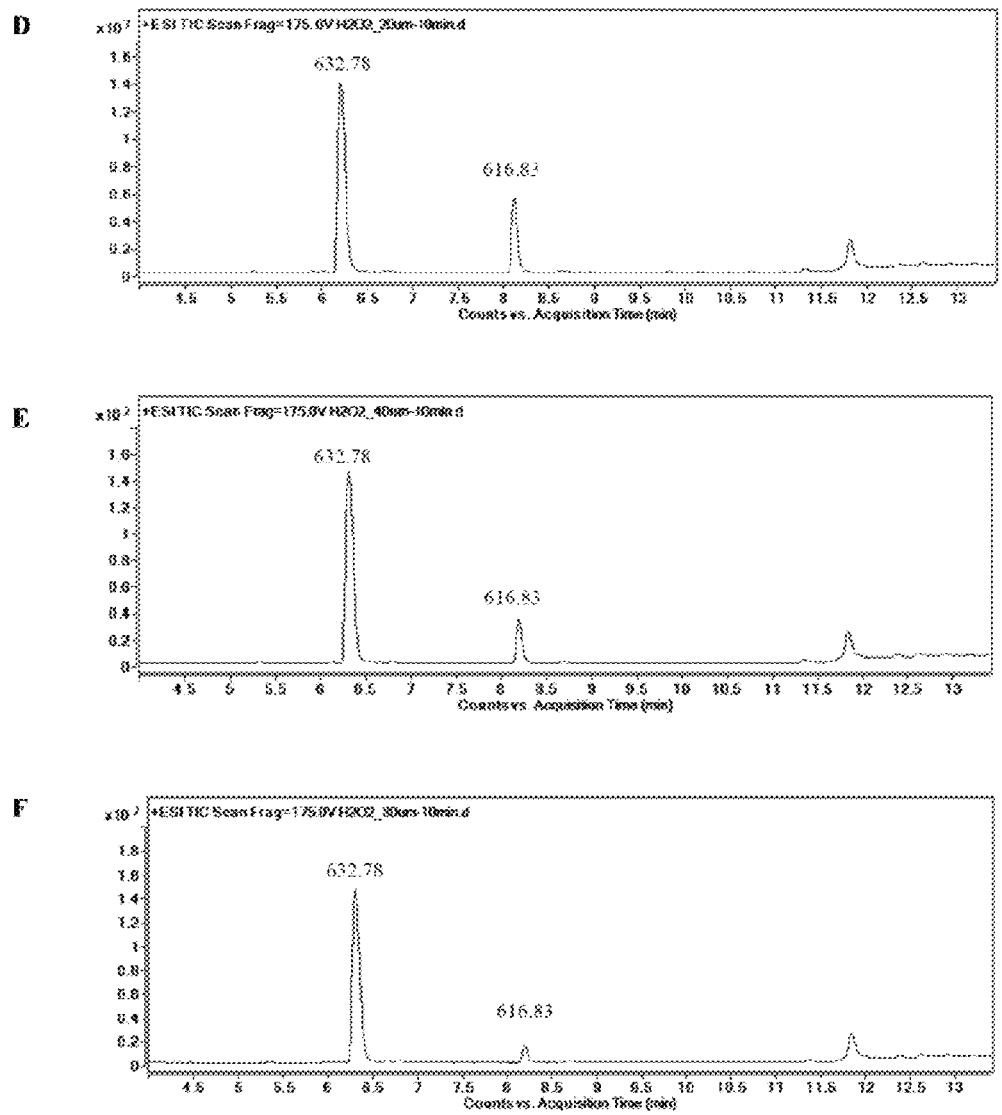
Figure 4:
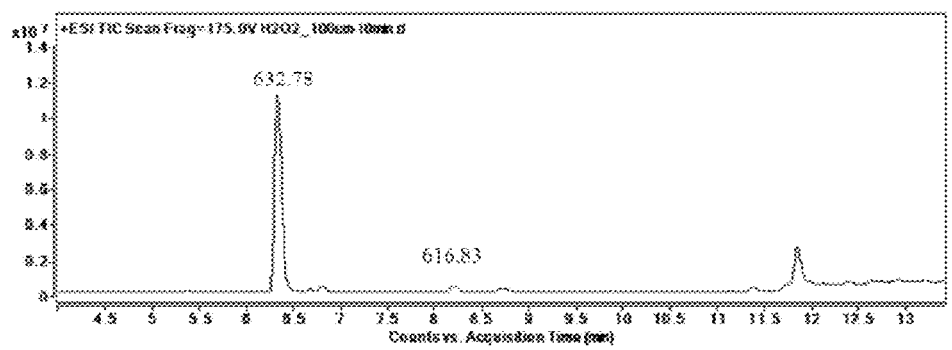

Oxidization of Methionine in Short EGFR Peptide by H₂O₂ in a Dose- and Time-Dependent Manner The methionine amino acid of a short EGFR peptide containing the T790M mutation could be easily oxidized in a dose-dependent manner under oxidative stress condition. This example shows that the main reason for EGFR protein degradation is due to specific oxidation on methionine amino acid residue at peptide position 790, eventually leading to EGFR protein damage, degradation and apoptosis specifically happening in T790M-containing NSCLC cells or host cells transfected with T790M construct. A peptide equivalent to the amino acid sequence position from 788 to 792 of EGFR in wild-type (LITQL) and T790M mutant (LIMQL) of EGFR (Sequence acquired from Pubmed database; SEQ. ID. NO. 2/GenBank Accession number of amino acid is NP_005219) is synthesized and both of them are subject to mass spectrometry. In FIG. 4A, ESI-MS detects the standard peptide of LIMQL and oxidized form of the peptide (LIM(O)QL). They are used as standard of the MS pattern of the un-oxidized form of methionine ("M") and the oxidized form methionine ("M(O)") for the EGFR short peptide. FIG. 4B-G are ESI-MS results of oxidized methionine in peptide treated with different concentrations of $H_2O_2$: FIG. 4B is for $H_2O_2$ untreated sample; FIG. 4C is for sample treated with 10 µM $H_2O_2$ for 10 min; FIG. 4D is for sample treated with 20 µM $H_2O_2$ for 10 min; FIG. 4E is for sample treated with 40 µM $H_2O_2$ for 10 min; FIG. 4F is for sample treated with 80 µM $H_2O_2$ for 10 min; FIG. 4G is for sample treated with 100 µM $H_2O_2$ for 10 min. One of representative data is shown (n=3). The result in FIG. 4 indicates that the short EGFR peptide containing un-oxidized form T790M can be oxidized by ROS in a time- and dose-dependent manner.

Example 6

Figure 5:
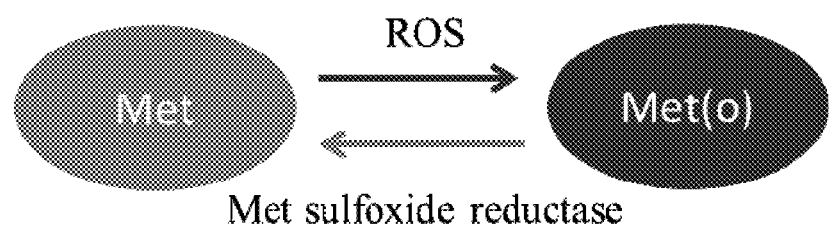
FIG. 5 is a schematic diagram showing how methionine is oxidized or reduced by ROS and reductase in the proposed signaling pathway.
Figure 6:
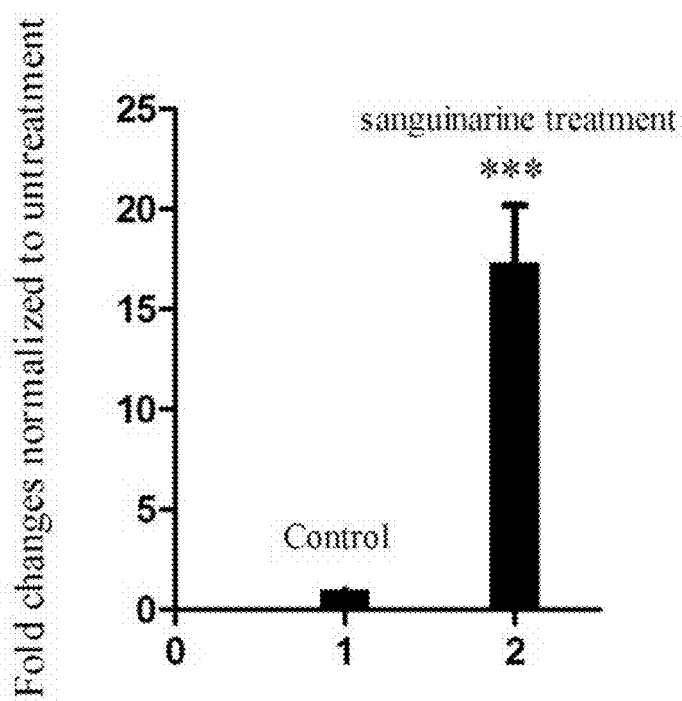
FIG. 6: (A) RNA expression level of NOX 3 compared in cells treated with or without sanguinarine. Results are expressed as mean±S.E.M. The data represent mean±S.E.M. of three independent experiments. (n=3, ***p<0.001); (B) Up-regulation of NOX 3 by sanguinarine on protein level; (C) Degradation of EGFR induced by sanguinarine in H1975 at 24 hrs. One of representative data was shown (n=3); (D) Real-time PCR detected RNA expression level of Msr A in 5 NSCLC cell lines. The expression level of Msr in other 5 cell lines is normalized to that of BEAS-2B. The data represent mean±S.E.M. of three independent experiments (n=3, *p<0.05, p<0.01, *p<0.001).
Figure 6:
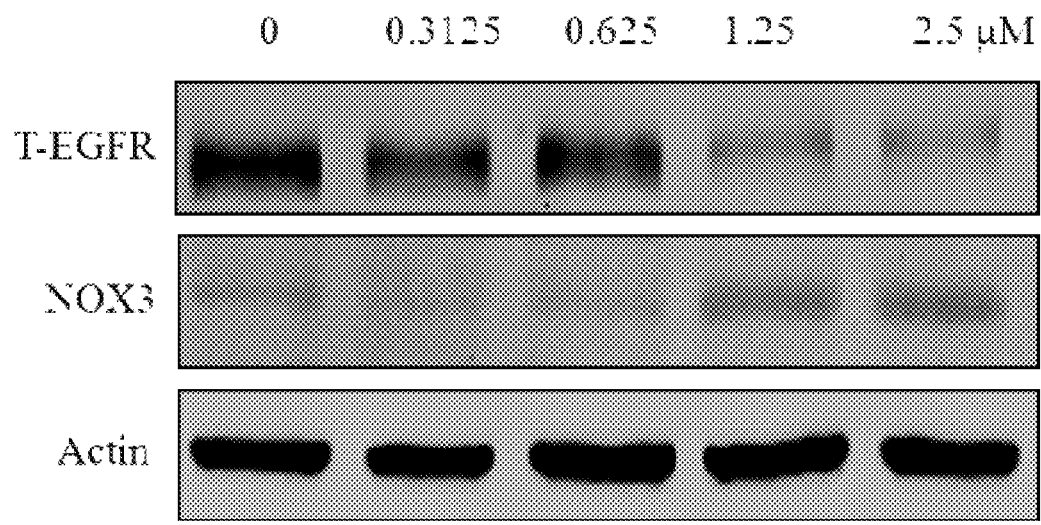
Figure 6:
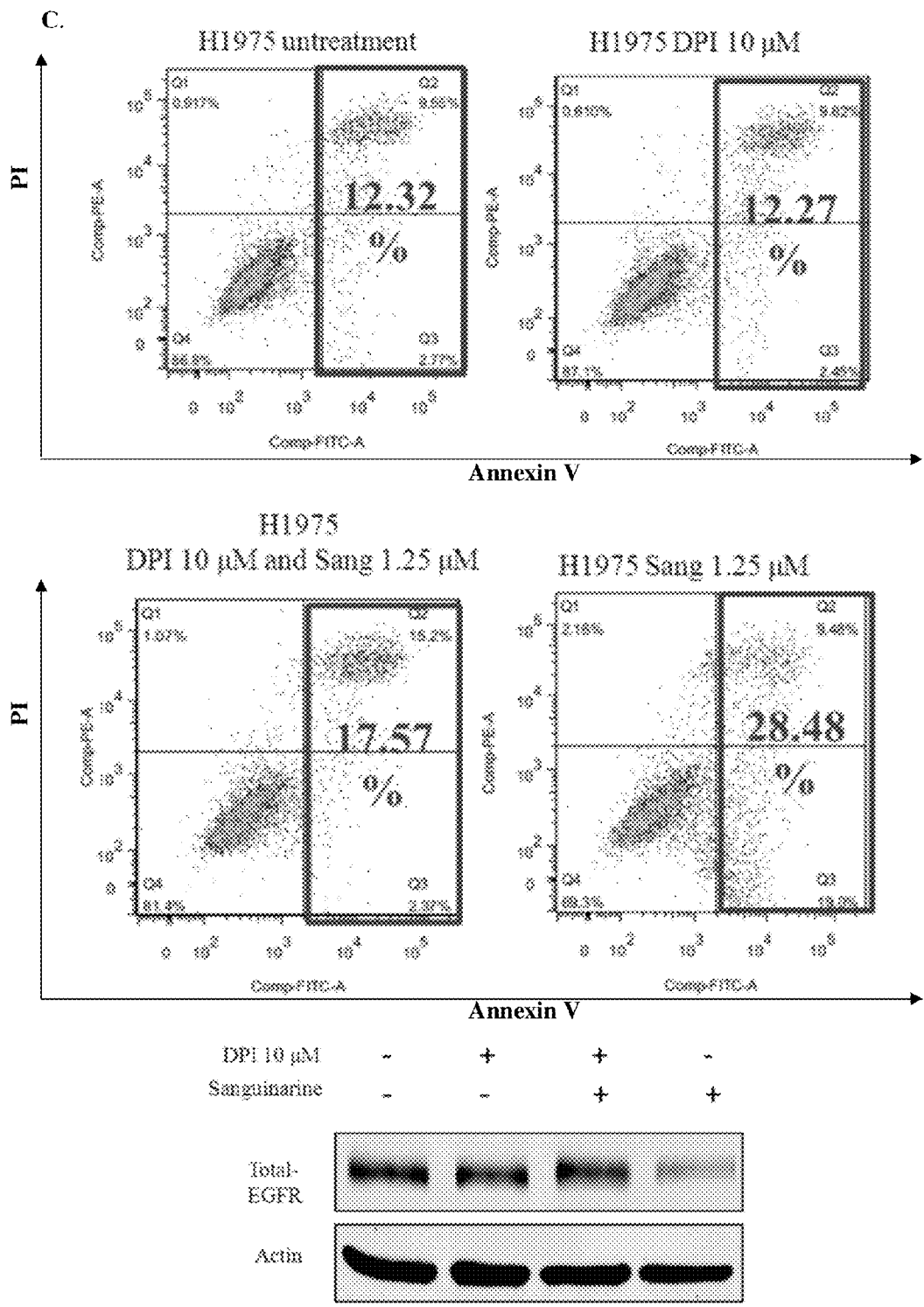
Figure 6:
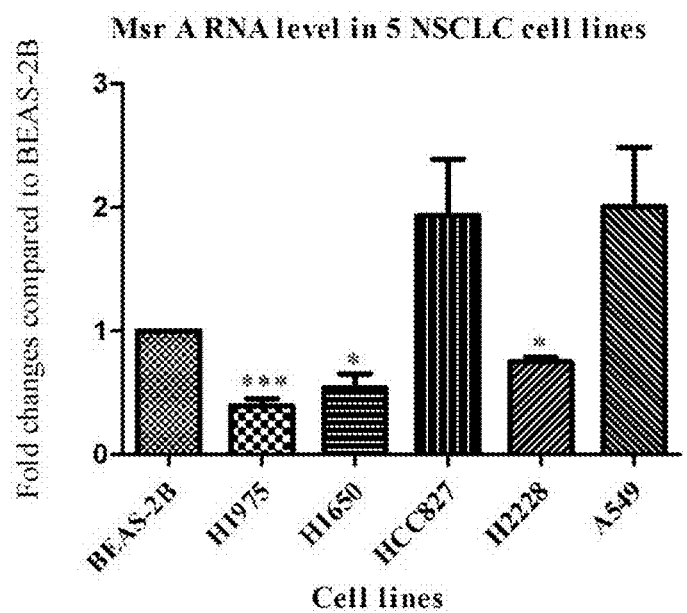
Figure 7:
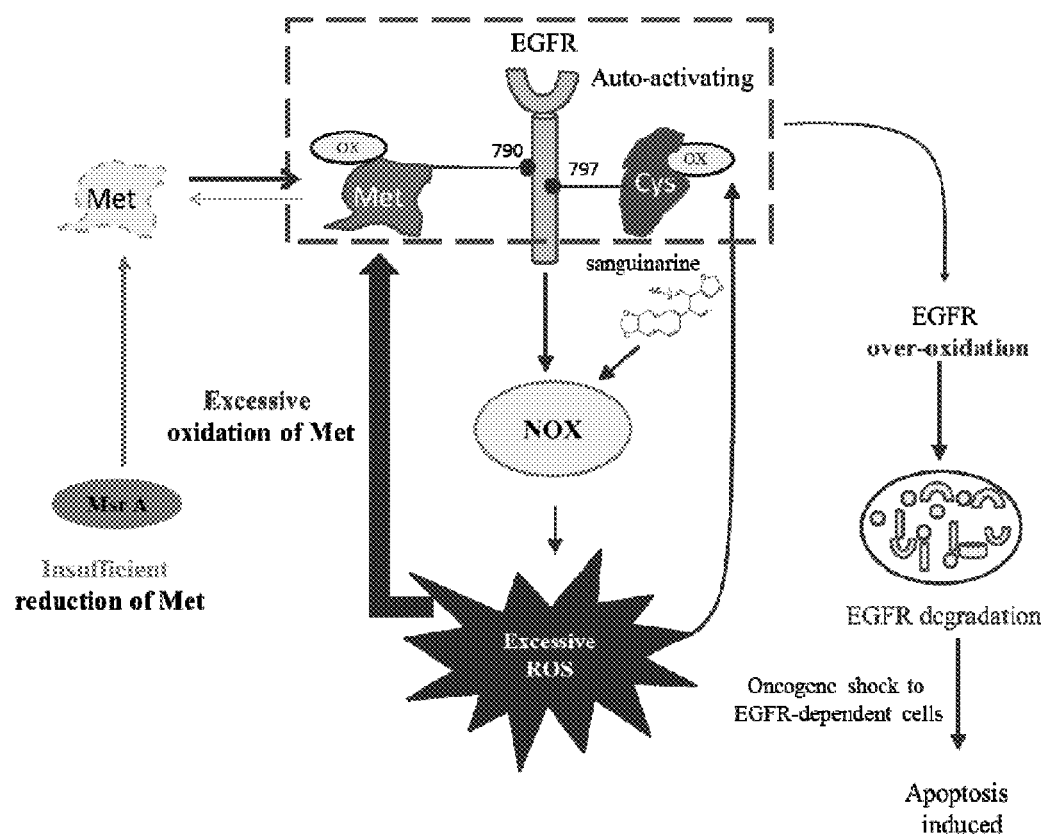
FIG. 7 is schematic diagram of the proposed cell model of H1975 cells in EGFR degradation induced by sanguinarine and $H_2O_2$.

Effect of Sanguinarine on RNA and Protein Expression of NOX 3 in H1975 Cells In this example, the results demonstrate that sanguinarine increases the expression of NOX 3 in both RNA and protein level in H1975 cells. FIG. 6A shows the RNA expression level of NOX 3 in cells treated with and without sanguinarine. The fold change of treated group is normalized to untreated group. Results are expressed as mean±S.E.M. The data represent mean±S.E.M. of three independent experiments. (n=3, ***p<0.001). In FIG. 6B, the up-regulation of NOX 3 by sanguinarine is also confirmed on protein level, which is corresponding to the degradation of EGFR. The flow cytometry result in FIG. 6C supports that DPI blocks the apoptosis and the degradation of EGFR induced by sanguinarine in H1975 at 24 hrs. One of representative data is shown (n=3). FIG. 6D uses real-time PCR to detect the RNA expression level of Msr A in five NSCLC cell lines. The expression level of Msr in other 5 cell lines is normalized to that of BEAS-2B cell line. The data represent mean±S.E.M. of three independent experiments (n=3, *p<0.05, p<0.01, *p<0.001). The result in this example supports that NADPH oxidase and methionine sulfoxide reductase are key enzymes involved in the ROS generation induced by reactive oxygen species stimulation in gefitinib-resistant NSCLC. Schematic diagram of how methionine (Met) is oxidized by NADPH oxidase (ROS) and reduced by methionine sulfoxide reductase is shown in FIG. 5. FIG. 7 is a cell model further illustrating how sanguinarine and $H_2O_2$ act on the signaling pathway of inducing EGFR degradation in H1975 cells, and thereby leading to apoptosis of the cells. H1975 cells contain L858R and T790M double mutation on EGFR which can auto-activate EGFR without the stimulation of EGF and thus continually activates NOX family and generates high basal ROS level. Like A549, ROS produced by NOX oxidizes (OX) the cysteine (Cys) residue at position 797 of EGFR and further activates EGFR to promote cell proliferation. Besides oxidation at Cysteine 797, Methionine (Met) residue at position 790 site of EGFR is also easily to be oxidized. Msr A, which is the intracellular reduction enzyme, can reduce the oxidized Met form back to original reduced form, is lowly expressed in H1975. However, due to mild basal oxidation, it can still reduce Met back to reduce from. However, under high basal ROS level and low basal anti-oxidation capacity of Met, treatment with sanguinarine can push the intracellular ROS level beyond the upper limit, and Msr A is insufficient to reverse the excessive oxidation on Met. As a result, EGFR in H1975 is over-oxidized and subsequently damaged. The degradation of EGFR results in oncogene shock to EGFR-dependent H1975 cells and finally apoptosis is induced.

INDUSTRIAL APPLICABILITY

The presently claimed methods are useful in drug discovery and design of treatment strategy for selective targeting Gefitinib-resistant non-small-cell lung cancer harboring T790M mutation by using agent elevating reactive oxygen species to induce methionine oxidation. The presently disclosed sanguinarine and other agent that release high ROS exerts specific remarkable cytotoxic effect on killing Gefitinib-resistant NSCLC cell. The ability of sanguinarine and other agents in inducing high ROS levels can effectively and specifically trigger the degradation of EGFR in T790M containing NSCLC, resulting in apoptosis. The low basal expression level of methionine reductase in T790M containing NSCLC cell lines suggests that sanguinarine can be used as cytotoxic agent to kill T790M-containing NSCLC by causing oxidation of methionine, which can be developed into a methionine reductase inhibitor to enhance the damage to T790M EGFR protein to basal oxidase stress. Also, NOX3 are upregulated by sanguinarine, indicating that NOX3 activator can be used as new drug to treat T790M containing NSCLC patients by elevation of ROS. Taken together, the present invention indicates that sanguinarine and any other agents that release high level of ROS can be used for further investigation as new class of EGFR inhibitor by directing oxidized the sulphur atom containing amino acid residues of EGFR, such as methionine and potentially on cysteine, which are the only two essential amino acids containing S atom that could be oxidized, resulting in EGFR protein damage. These agents can be used to act against Gefitinib-resistant NSCLC patients, especially for the group of patients with EGFRL858R+T790M mutation which represents 49% of all Gefitinib resistance cases. This novel strategy to block EGFR growth signaling pathway in NSCLC based on protein oxidation method is completely new idea as the currently clinically available inhibitors or inhibitors undergoing clinical trials are based on inhibition of EGFR phosphorylation rather than specifically inducing methionine oxidation and EGFR degradation.

The foregoing description of the present invention has been provided for the purposes of illustration and description. It is not intended to be exhaustive or to limit the invention to the precise forms disclosed. Many modifications and variations will be apparent to the practitioner skilled in the art.

The embodiments are chosen and described in order to best explain the principles of the invention and its practical application, thereby enabling others skilled in the art to understand the invention for various embodiments and with various modifications that are suited to the particular use contemplated. It is intended that the scope of the invention be defined by the appended claims and their equivalence.

REFERENCE

1. Jemal, A., et al., *Cancer statistics, 2010*. CA: a cancer journal for clinicians, 2010. 60(5): p. 277-300.
2. Chang, A., *Chemotherapy, chemoresistance and the changing treatment landscape for NSCLC*. Lung cancer, 2011. 71(1): p. 3-10.
3. Tam, I. Y., et al., *Double EGFR mutants containing rare EGFR mutant types show reduced in vitro response to gefitinib compared with common activating missense mutations*. Molecular cancer therapeutics, 2009. 8(8): p. 2142-51.
4. Leung, E. L., et al., *SRC promotes survival and invasion of lung cancers with epidermal growth factor receptor abnormalities and is a potential candidate for molecular-targeted therapy*. Molecular cancer research: MCR, 2009. 7(6): p. 923-32.
5. Wong, D. W., et al., *The EML4-ALK fusion gene is involved in various histologic types of lung cancers from nonsmokers with wild-type EGFR and KRAS*. Cancer, 2009. 115(8): p. 1723-33.
6. Jun, H. J., et al., *The oncogenic lung cancer fusion kinase CD74-ROS activates a novel invasiveness pathway through E-Syt1 phosphorylation*. Cancer research, 2012. 72(15): p. 3764-74.
7. Ono, M. and M. Kuwano, *Molecular mechanisms of epidermal growth factor receptor (EGFR) activation and response to gefitinib and other EGFR-targeting drugs*. Clinical cancer research: an official journal of the American Association for Cancer Research, 2006. 12(24): p. 7242-51.
8. Sequist, L. V., et al., *Genotypic and histological evolution of lung cancers acquiring resistance to EGFR inhibitors*. Science translational medicine, 2011. 3(75): p. 75ra26.
9. Beuria, T. K., M. K. Santra, and D. Panda, *Sanguinarine blocks cytokinesis in bacteria by inhibiting FtsZ assembly and bundling*. Biochemistry, 2005. 44(50): p. 16584-93.
10. Obiang-Obounou, B. W., et al., *The mechanism of action of sanguinarine against methicillin-resistant Staphylococcus aureus*. The Journal of toxicological sciences, 2011. 36(3): p. 277-83.
11. Pencikova, K., et al., *Investigation of sanguinarine and chelerythrine effects on LPS-induced inflammatory gene expression in THP-1 cell line*. Phytomedicine: international journal of phytotherapy and phytopharmacology, 2012. 19(10): p. 890-5.
12. Niu, X., et al., *The anti-inflammatory effects of sanguinarine and its modulation of inflammatory mediators from peritoneal macrophages*. European journal of pharmacology, 2012. 689(1-3): p. 262-9.
13. Vrba, J., E. Orolinova, and J. Ulrichova, *Induction of heme oxygenase-1 by Macleaya cordata extract and its constituent sanguinarine in RAW264.7 cells*. Fitoterapia, 2012. 83(2): p. 329-35.
14. Vrba, J., et al., *Sanguinarine is a potent inhibitor of oxidative burst in DMSO-differentiated HL-60 cells by a non-redox mechanism*. Chemico-biological interactions, 2004. 147(1): p. 35-47.
15. Bai, L. P., et al., *Site-specific binding of chelerythrine and sanguinarine to single pyrimidine bulges in hairpin DNA. Analytical and bioanalytical chemistry*, 2008. 392 (4): p. 709-16.

The foregoing references are also incorporated herein by reference in their entirety.

What is claimed is:

1. A method for examining cytotoxic potency of a compound or chemical agent for selectively inducing cytotoxicity in Gefitinib-resistant non-small-cell lung cancer harboring T790M mutation comprising providing Gefitinib-resistant non-small-cell lung cancer cells harboring said mutation or transfecting into normal cells with an expression vector containing a construct of epidermal growth factor receptor having said mutation; applying an effective amount of said compound or chemical agent to either said cancer cells or normal cells transfected with said expression vector, wherein the cytotoxic potency of said compound or chemical agent is indicated by an elevating level of reaction oxygen species through up-regulation and activation of NOX3 which triggers degradation of epidermal growth factor receptor and leads to apoptosis of said cancer cells.

2. The method of claim 1, wherein said compound is sanguinarine.

3. The method of claim 1, wherein said chemical agent is hydrogen peroxide.

4. The method of claim 1, wherein said cancer cells are H1975 cells.

5. The method of claim 1, wherein said normal cells are HEK293 cells.

6. The method of claim 1, wherein said construct of epidermal growth factor receptor having said mutation has a coding sequence of SEQ. ID NO. 1.

7. The method of claim 1, wherein said epidermal growth factor receptor with the T790M mutation has an amino acid sequence of SEQ. ID. NO. 2.

8. The method of claim 1, wherein said compound is a methionine reductase inhibitor.

9. The method of claim 1, wherein said compound is a NOX3 activator.

* * * * *